United States Patent [19]

McFadden et al.

[11] Patent Number: 4,568,747

[45] Date of Patent: Feb. 4, 1986

[54] PROCESS FOR MAKING 2-AMINOETHYL ETHER

[75] Inventors: Russell T. McFadden, Freeport; William P. Coker, Lake Jackson, both of Tex.

[73] Assignee: The Dow Chemical Company, Midland, Mich.

[21] Appl. No.: 316,613

[22] Filed: Oct. 30, 1981

[51] Int. Cl.$^4$ ............................................. C07D 295/00
[52] U.S. Cl. ................................ 544/358; 260/239 E; 564/511
[58] Field of Search .................... 260/239 E; 544/358; 564/511

[56] References Cited

U.S. PATENT DOCUMENTS 4,083,873 4/1978 Sherrod et al. ...................... 564/511

Primary Examiner—Glennon H. Hollrah
Assistant Examiner—James H. Turnipseed
Attorney, Agent, or Firm—Melvin W. Barrow

[57] ABSTRACT

The invention is a process for obtaining pure BAEE from the crude reaction mixture of $H_2SO_4$ and monoethanolamine. It consists of five major operations, which are:

1. Separation of 2-aminoethyl hydrogen sulfate (AEHS) from $BAEE.2H_2SO_4$ by mixing the molten crude product with crushed ice and filtering out the resulting AEHS which precipitates;
2. precisely neutralizing the acidity in the filtrate with alkali or alkaline earth hydroxides, NaOH to form $Na_2SO_4$ and free BAEE;
3. extracting the BAEE and small amounts of other amines from this neutralized solution with an alcohol solvent having limited solubility in water, such as n-butanol;
4. concentrating the amine extract by precipitating the amines in a separate, liquid layer by saturating the extract with carbon dioxide gas; and
5. obtaining pure BAEE from this concentrate by distillation (at atmospheric pressure through an efficient distillation column).

1 Claim, No Drawings

PROCESS FOR MAKING 2-AMINOETHYL ETHER

BACKGROUND OF THE INVENTION

Previous processes for preparing bis(2-aminoethyl) ether (BAEE) conducted hydrolysis of the crude product of the dehydration of ethanolamine. Such processes resulted in a by-product which caused difficulties in distillation to recover the BAEE.

BRIEF DESCRIPTION OF THE INVENTION

The invention is a process for obtaining pure BAEE from the crude reaction mixture of $H_2SO_4$ and monoethanolamine. It consists of five major operations, which are:
1. Separation of 2-aminoethyl hydrogen sulfate (AEHS) from BAEE.$2H_2SO_4$ by mixing the molten crude product with crushed ice or an equal amount of refrigerated water at 1°-24° C. and filtering out the resulting AEHS which precipitates;
2. precisely neutralizing the acidity in the filtrate with alkali or alkaline earth hydroxides (e.g. NaOH) to form $Na_2SO_4$ and free BAEE;
3. extracting the BAEE and small amounts of other amines from this neutralized solution at not less than 35° C., with a suitable water-saturated solvent, such as n-butanol, i-butanol, pentanol, i-pentanol, sec. pentanol or hexanol, n-butanol being preferred;
4. concentrating the amine extract by precipitating the amines in a separate, liquid layer by saturating the extract with carbon dioxide gas; and
5. obtaining pure BAEE from this concentrate by distillation, preferably at atmospheric pressure, through an efficient distillation column.

DETAILED DESCRIPTION OF THE INVENTION

Example

Step 1

To a clean, dry, five-liter glass reactor was charged 2718 gm. of 96.1% sulfuric acid (26.7 mols) and to this, with stirring and cooling, was added 1556 gm. of 98.3% monoethanolamine (25.1 mols). The rate of addition was regulated so as to hold the temperature below 110° C. with the acid container in an ice-water bath. When the addition was complete (100 minutes), heat was applied to the reactor with an electric mantle to distill water. The amount of water to be collected was calculated as follows:

Vol. of Distillate at 25° C. to be collected, ml=(100.0-% purity of $H_2SO_4$)(weight of $H_2SO_4$)($10^{-2}$)+(100.0-% purity of MEA)(weight of MEA)($10^{-2}$)+(mols of MEA)(18.0)($\frac{1}{2}$)=358 ml When the reactor contents reached about 160° C., evolution of water began and the temperature of the boiling mixture rose slowly until it reached 215° C., where it was controlled. At this point a slow stream of nitrogen was used to carry over water until 363 ml of liquid was collected. The mixture was held at 210°-215° C. for one hour more.

Step 2

The crude product from Step 1 was cooled to 125°-130° C. and poured over 2594 gms of crushed ice in a two-gallon, plastic bucket, while vigorously stirring the contents of the bucket. After all of the crude product has been added, stirring was continued until no particles of amorphous "tar" (cold crude product) were found. The final temperature of the mixture was below about 30° C.

The contents of the bucket were poured over a large, course, fritted-glass filter and the filter cake, a gray, grainy mass, was allowed to suck dry.

Step 3

The potentiometric titration of the filtrate (5099 gm) gave two inflections, the first for free sulfuric acid and bisulfate, the second for protonated amines, including AEHS. In order for the extraction to be operated optimally, all of this acidity must be just neutralized, but no more:

a. $H_2SO_4 + 2\ OH^- \rightarrow 2\ H_2O + SO_4^=$
b. $HSO_4^- + OH^- \rightarrow H_2O + SO_4^=$
c. $R-NH_3^+ + OH^- \rightarrow H_2O + R-NH_2$
d. $N^+H_3-C_2H_4OSO_3^- + OH^- \rightarrow H_2O + NH_2-C_2H_4OSO_3^-$ The total acidity of the filtrate, expressed as milliequivalents per gram (meq/gm) was used to calculate the quantity of aqueous sodium hydroxide required to carry out the above reactions.

Wt. of 20% NaOH required=wt. of filtrate×meq of acidity/gm×40.0×1/(10×exact concentration of aqueous NaOH, weight %)

The calculated amount of aqueous 20% NaOH was added slowly to the filtrate with stirring and sufficient cooling to hold the temperature below 50° C. The resulting nearly-black solution was then filtered to remove a trace of insoluble black solid, and sent to the extractor. (Note: The pH of this just-neutralized material is a function of the amine content, and ranges from about 11½ to 12½.)

At this point, since no laboratory-scale, countercurrent extractor was available, data from an earlier study done in a 2.0- inch i.d. × 10 foot tall column (¼" saddle packing) were used to calculate the composition of an extract obtained from the above neutralized filtrate. It was assumed that, in actual operations, an efficient enough column would be used to reduce the MEA content of the raffinate to 0.1% or less. The calculated weight and composition of the extract was, therefore, made up and saturated with carbon dioxide by adding dry ice until a constant weight was obtained. The gain in weight corresponded closely to 1.0 mol of carbon dioxide absorbed per equivalent of amine present. The reaction is assumed to be:

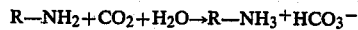

$$R-NH_2 + CO_2 + H_2O \rightarrow R-NH_3^+ HCO_3^-$$

The saturated mixture was allowed to stand for two hours, during which most of the amine bicarbonate-water phase settled to the bottom. It was collected with a siphon and distilled.

Step 4

The distillation apparatus for this operation was two thirty-tray Oldershaw columns in series. Both columns were equipped with variable-reflux, liquid take-off heads, the reflux ratio of each column being independently controlled. The still-pot for the first column was a three-liter, spherical, Pyrex flask and that for the second, a two-liter flask of the same kind. All of the amine carbonate solution was charged to the first still and heated at 65-70 volts of mantle power. The liquid reflux was set at 50%. As liquid from this column left the head it was conducted down a three-eighths inch i.d. glass pipe and into the second still-pot. As liquid distillate collected in this vessel, power to the heating mantle was applied gradually so that the second column was brought into operation without super-heating. Steady-state operating conditions are given below.

Fractional Distillation of the Crude Aqueous Amine Bicarbonate Concentrate

| Cut | Mantle Power | | Reflux, % | |
|---|---|---|---|---|
| | #1 Col. | #2 Col. | #1 Col. | #2 Col. |
| water/n-BuOH | 70 v. | 55 v. | 50 | 50 |
| MEA/BAEE | 75 | 90 | 90 | 90 |
| BAEE | 75–85 | 95–105 | 50–0 | 50 |

Under these conditions, 80–81% of the BAEE fed to the first still was recovered as distillate of 99.0% minimum purity, and 17% was recovered as an impure fraction mixed with ethanolamine. Subsequent work showed that, for the composition charged to the #1 still, 32 theoretical plates would have given a 93% recovery of the BAEE as 99.0% pure distillate at 95% reflux.

Step 5

The weight of filter cake from Step 2 and its analyzed purity were used to calculate the amount of cold 20% aqueous NaOH required to dissolve the AEHS as its sodium salt and to fully neutralize the sulfuric acid held on the filter cake.

f.  $NH_3^+\text{—}C_2H_4OSO_3^- + NaO^+H^- \rightarrow NH_2\text{—}C_2H_4OSO_3^-Na^+ + H_2O$ g.  $H_2SO_4 + 2\ NaO^+H^- \rightarrow 2\ Na^+SO_4^= + 2\ H_2O$ h.  $HSO_4^{31} + NaO^+H^- \rightarrow 2\ Na^+SO_4^= + H_2O$ Reaction 'f'

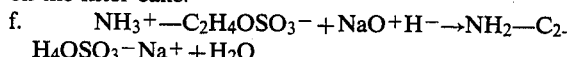
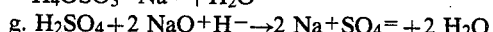
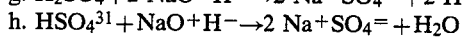

was found to be distinctly endothermic.

The resulting clear solution was added dropwise to a boiling solution of 14% aqueous NaOH, the amount of NaOH in the vessel being sufficient for the reaction

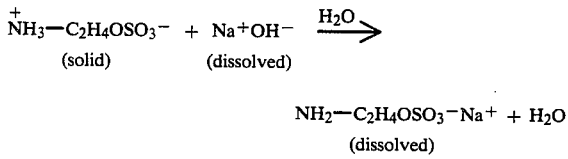

As the ethylenimine formed, it codistilled with water through a 30-tray Oldershaw column and was collected as a 14–15% solution in water. The column was fitted with a small feed tank at the top, from which a 31% aqueous NaOH solution was allowed to trickle down the inside of the distillation column. Without this, the yield of EI in the distillate was severely reduced.

The filter cake from Step 2 weighed 1525 gm. It was titrated in water with 1.0N NaOH and found to contain 8.76 equivalents of weak acid and 1.23 equivalents of strong acid, 9.99 acid equivalents in all. By liquid chromatography, the filter cake assayed 73% AEHS. It was dissolved by mixing it with 2089 gm of 19.0% aqueous NaOH in a battery jar (9.91 equivalents of base).

To the ethylenimine reactor/still was charged 163.0 gm of 19.4% aqueous NaOH (7.90 equivalents) and to the overhead dropping funnel, 441 gm of 32.3% aqueous NaOH (3.56 equivalents). The total NaOH added was 21.37 equivalents. The NaOH required for neutralization plus ring closure was calculated as:

1. neutralization 9.91 equivalents
2. ring closure (1525 gm)(0.73)/141 gm/equiv. = 7.90 equivalents or 17.81 equivalents in all. Therefore, the NaOH added to the filter cake plus that charged to the reactor/still was equal to the total base demand, and that dripped down the column was excess by 20%.

The aqueous NaOH in the reactor/still was brought to boiling (110° C.), the NaOH solution in the overhead feed tank was begun flowing, and addition of the sodium aminoethyl sulfate (NaAES) solution to the boiling reactor/still was started. As the distillation proceeded, the boiling temperature of the reactor/still liquid fell slowly to 102° C., then gradually rose again. About half-way through the procedure, it became necessary to add an additional 600 ml of water to dissolve solid sodium sulfate. The distillate consisted of 1764 gm (1783 ml of liquid containing 204 gms of ethylenimine and 2.0 gm of N(2-aminoethyl)-aziridine. This represents an EI yield of 59.3% based on AEHS in the filter cake. A similar preparation starting with filter cake containing 84% AEHS yielded 74.8% ethylenimine. The distillation residue from this second preparation contained the amines shown below.

| Amine | Concentration in Distillation Residue |
|---|---|
| ethanolamine | 0.73% |
| BAEE | 0.57 |
| EI | 0.51 |
| aminoethyl aziridine | 0.42 |
| piperazine | 0.09 |

We claim:

1. A process for producing bis(2-aminoethyl) ether BAEE) and ethylenimine (EI) by forming a crude reaction product by the addition of ethanolamine to sulfuric acid at a temperature below about 100° C. over about a 100 minute period and thereafter raising the temperature to remove the water of reaction, separating the crude 2-aminoethyl hydrogen sulfate (AEHS) by cooling to below 30° C. and filtering the solids which form, and thereafter titrating the filtrate to neutral with
    aqueous sodium hydroxide at a temperature below 50° C. with stirring and recovering any solid and the filtrate carbonated to about 1 mole carbon dioxide per equivalent of amine, thereafter collecting the lower amine bicarbonate-water phase which settles and distilling the same at above 50% reflux to recover a water cut, a MEA/BAEE cut and a 99.0+ pure cut of BAEE;
    neutralizing the AEHS solids with cold sodium hydroxide then dropped into a boiling sodium hydroxide solution thereby to convert the AEHS to EI by co-distillation with water while countercurrently trickling 14–15% sodium hydroxide to the EI-water distillate rising in the column.

* * * * *